United States Patent [19]

Broadnax, Jr.

[11] Patent Number: 4,976,684
[45] Date of Patent: Dec. 11, 1990

[54] METHOD OF USING A BENDABLE TROCAR

[75] Inventor: Cecil H. Broadnax, Jr., Somerset, N.J.

[73] Assignee: Johnson & Johnson Orthopaedics, Inc., New Brunswick, N.J.

[21] Appl. No.: 470,184

[22] Filed: Jan. 24, 1990

Related U.S. Application Data

[63] Continuation of Ser. No. 273,547, Nov. 21, 1988, abandoned.

[51] Int. Cl.$^5$ .............................................. A61M 27/00
[52] U.S. Cl. .................................... 604/51; 604/272; 606/223; 223/102
[58] Field of Search ........ 606/185, 222, 223, 224–227, 606/108; 604/272, 51; 223/102; 112/222

[56] References Cited

U.S. PATENT DOCUMENTS

| | | | |
|---|---|---|---|
| 2,240,330 | 4/1941 | Flagg et al. | 128/339 |
| 2,899,960 | 8/1959 | Ginsburg | 604/272 |
| 3,197,997 | 8/1965 | Kurtz | 128/339 X |
| 4,010,756 | 3/1977 | DuMont et al. | 128/339 X |
| 4,140,125 | 2/1979 | Smith | 128/339 X |
| 4,359,053 | 11/1982 | Benjamin | 128/339 |
| 4,398,910 | 8/1983 | Blake et al. | 604/93 |
| 4,799,484 | 1/1989 | Smith et al. | 128/339 |

FOREIGN PATENT DOCUMENTS 2623796  6/1977  Fed. Rep. of Germany ...... 112/222

Primary Examiner—Michael H. Thaler
Attorney, Agent, or Firm—Paul A. Coletti

[57] ABSTRACT

A trocar, used to introduce wound drain catheters is disclosed. The trocar have a reduce cross sectional area that allows the trocar to be bent by the user to a desired configuration.

7 Claims, 2 Drawing Sheets

METHOD OF USING A BENDABLE TROCAR

This is a continuation of application Ser. No. 273,547, filed Nov. 21, 1988 now abandoned.

FIELD OF THE INVENTION

The present invention relates to trocars or needles which are used to thread or insert wound drainage catheters into the body of a surgical patient. The trocar of the present invention can be bent to the desired curvature prior to use.

BACKGROUND OF THE INVENTION

Wound drain catheters generally have a flexible drain portion and a flexible outflow tube portion. The drain portion is integral or attached to the outflow portion. The drain portion is placed in or adjacent the wound site and the outflow portion will pass through the skin of the patient and be connected to a source of vacuum to drain the wound site.

Trocars are commonly used to insert wound drainage catheters or tubing into a drainage site adjacent a surgical wound or from a surgical wound site through the skin of a patient. These trocars usually have the catheter or tubing attached to the one end of the trocar so that the tubing follows the trocar along a path through the patient's body.

Several techniques may be used to insert a wound drain catheter in the patient's body. For example, a surgeon may simply place the drain portion and a small part of the outflow tube portion in the wound, close the incision, and suture around the outflow tube Portion. This technique is somewhat unsatisfactory, since it is difficult to completely seal the area around the outflow tube by suturing, and thus, the wound may become infected. A more satisfactory technique is to pass a trocar, preattached to the end of the outflow tube, through healthy tissue by entering the patient's body at a point within the wound and exiting at a point adjacent to the wound. The surgeon pulls the outflow tube portion through the tissue with the trocar until the catheter is properly positioned, with the drain in the wound. Since the outflow tube exits the body at a point adjacent the wound, the wound can be completely closed by suturing, thereby reducing the risk of infection.

The trocars are manufactured with a slight bend near the pointed end to allow them to be manipulated through the skin of the patient. The catheter or drainage tubing will follow the path made by the trocar until the drainage end of the tubing is in its desired position within the body and the outflow portion of the catheter outside the patient's body. At that time the trocar will then be cut from the tubing and the tubing connected to a wound drain evacuator or a source of vacuum.

U.S Pat. No. 4,398,910 discloses the use of trocar in the manner described above.

U.S. Pat. No. 4,359,053 discloses the fastening of plastic tubing to a trocar or needle for the same purpose.

The trocars are usually made of very hard surgical grade stainless steel or other materials so that they may be sharpened to a very fine point to allow the distal end or sharpened end of the trocar to pass through the body tissue. There is generally a slight bend, about 15°, in the trocar when manufactured as shown in U.S. Pat. No. 4,398,910 to allow the trocar to be manipulated through the body of the patient to correctly position the wound drainage tubing in the position desired by the surgeon.

In many instances, it is difficult to properly position the wound drainage tubing because it is difficult to pass the trocar through the patient's body without hitting a solid structure such as bone.

SUMMARY OF THE INVENTION

The present invention provides a trocar, normally used to insert wound drainage tubing into the body of a patient, which is capable of being readily bent by the surgeon to the configuration which is desired by the surgeon. This allows easier and more accurate insertion of the wound drain catheter in the desired location in the patient's body. The trocar has an area of reduced cross section which allows the trocar to be bent with a force which can be generated by the hands of the surgeon.

DETAILED DESCRIPTION OF THE INVENTION

Figure 1:
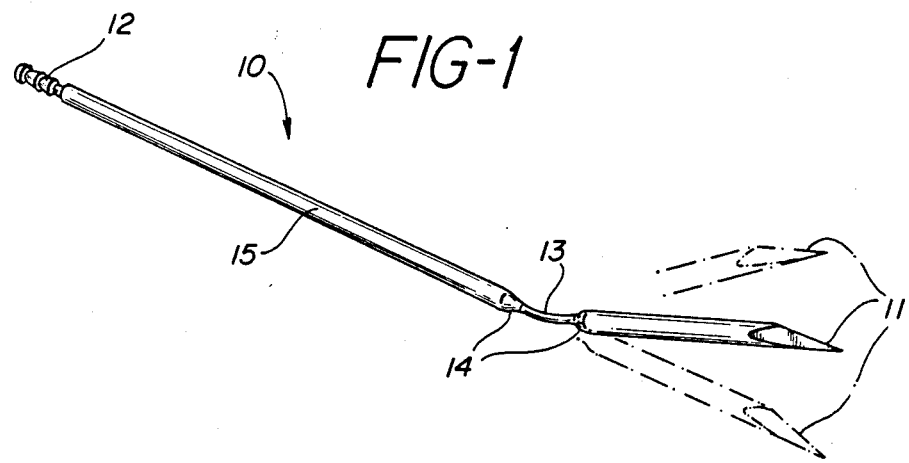
FIG. 1 shows the trocar of the present invention with the point of the trocar shown in phantom in two different positions.
Figure 2:
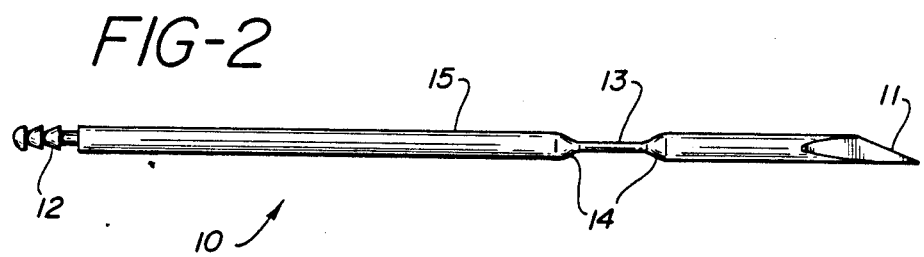
FIG. 2 shows the trocar of the present invention in a straight configuration.

The bendable trocar of the present invention comprises a generally circular shaft 10 which has a triangular point 11 at the distal end and a tubing attachment fixture 12 at the proximal end. At a location which is preferably between the midpoint of the trocar and the distal end there is a reduced cross section area 13 which is tapered at both ends 14. The trocar is generally made of a material which is capable of being sharpened to a fine point. The material is sufficiently hard to hold the point of the trocar. The trocar must also be capable of being sterilized before use. Although numerous materials would fit these criteria, such as malleable or bendable metals and including some hard plastic materials, the material of choice is a grade 303 stainless steel. The overall length of the trocar is commonly approximately six inches. The center of the reduced cross section area 13 is between two and two and three quarter inches 0.50–70 mm) from the distal end or pointed end of the trocar. This position can be varied, but generally, the reduced section should be no more than one-half of the distance between the distal end and the proximal end of the trocar. The reduction in the cross sectional area of the shaft of the trocar should be such that the trocar can be readily bent by the surgeon to the desired configuration. However, the trocar should not be so flexible that itself could bend upon hitting a hard object, such as a bone in the body when the trocar is in use. The trocar can be bent up to an angle of about 60° to 90° without breaking.

Trocar of the type used to insert wound drainage tubing or catheters have a diameter of from about 0.125 to 0.250 inches (3 to 65 mm) and a length of about 6 inches (150 mm). If the trocar has a diameter of about 0.125 inches or less, it can be bent without any reduction in its cross sectional area but it can be bent much more readily if the cross section is reduced. If the trocar has a diameter over about 0.150 inches (3.8 mm) it is difficult to bend. Reducing the cross section of the trocar to about 0.08 to 0.1 inches (2 to 2.5 mm) will allow the trocar to be bent to the desired configuration by the surgeon.

Generally, the amount of force desired to bend the trocar to the desired position is between 10 and 40 pounds, preferably 20 to 30 pounds. This amount of force can readily be exerted by a surgeon with his hands. The amount of reduction in the cross sectional area shaft is somewhere between 8% and 20%, but generally, with grade 303 stainless steel a reduced shaft diameter of approximately 3/32 of an inch, (2 to 3 millimeters), can readily be bent by the surgeon to the desired configuration. There is a taper 14 from the large diameter portion 15 to the reduced diameter portion 13 at each end of the reduced diameter portion. The taper 14 helps to prevent tissue from being caught in the reduced diameter section when the trocar is drawn through the tissue.

Figure 3:
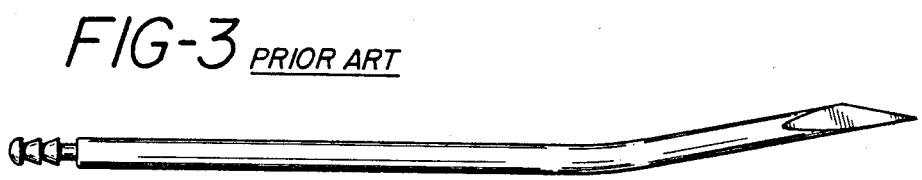
FIG. 3 shows the trocar of the prior art.

It should be noted that in the constant diameter of the prior art trocar shown in FIG. 3, is such that it is very difficult, if not impossible, to bend the shaft of the trocar to any great degree.

Figure 4A:
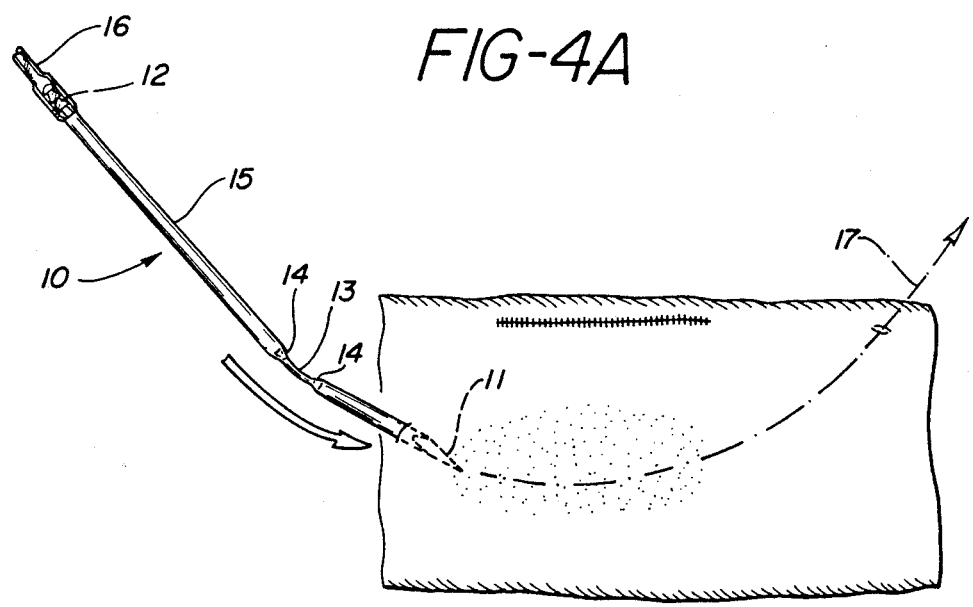
FIG. 4A shows the utilization of the trocar of the present invention and the intended path of the trocar through a body.
Figure 4B:
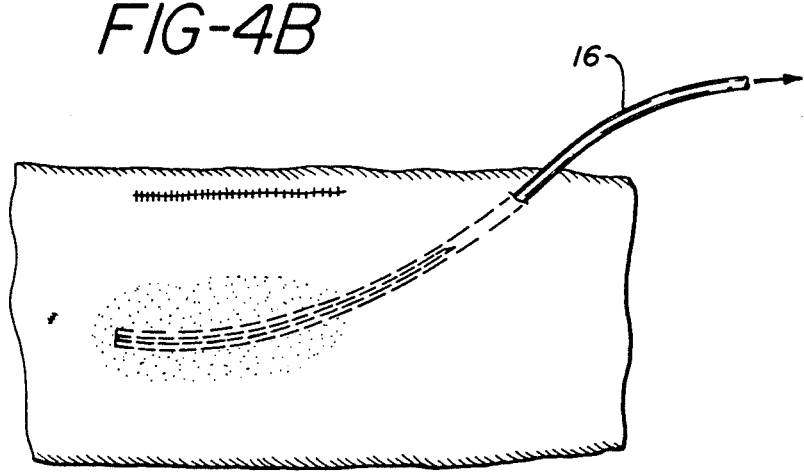
FIG. 4B shows the position of the wound drain catheter after it has been inserted in the body following the path of the trocar.

In use, as shown in FIGS. 4A and 4B, the catheter 16 would be attached to the proximal end of the trocar. The trocar would be bent to the desired configuration and passed through the surgical flap in the skin of the patient following a curved track as shown in the dotted line 17. Normally the trocar would be inserted through the patient's skin from the operative site. The catheter 16 would follow in the path of the trocar, and after the trocar had been removed from the patient the tubing would be placed in the correct position to drain the wound of the patient as shown in FIG. 4B. The trocar would then be cut from the tubing and the tubing inserted into a drain evacuator as well-known in the art.

I claim:

1. A method for draining fluids from humans comprising:
    attaching flexible tubing to a bendable trocar, said trocar having a rigid shaft with a solid generally uniform cross-section and a cutting edge on one end, means to attach said flexible tubing at the opposite end of said shaft, and said shaft having a portion of reduced cross-section relative to the generally uniform cross-section of said shaft to allow the shaft to be bent at the reduced cross-section by the user to an appropriate angle, up to about 90° without breaking through application of at least 10 pounds force, to allow the user to manipulate the trocar through the skin of said patient;
    bending said trocar to a generally convenient configuration, then passing said trocar through the skin of said patient, said trocar maintaining its bent shape while embedded in said patient's skin;
    passing said trocar out of the skin of said patient, while maintaining said flexible tubing within said patient's body; and
    draining fluid from the patient's body through said flexible tubing.

2. The method of claim 1 in which the cross-section of the shaft is circular.

3. The method of claim 2 in which the generally uniform circular cross-section has a diameter of about 0.125 inches to about 0.250 inches, and said reduced cross-section has a diameter of about 0.08 inches to about 0.1 inches.

4. The method of claim 3 in which the reduced cross-section is at a location between the midpoint of the shaft and its cutting edge.

5. The method of claim 3 in which the shaft is made of stainless steel.

6. The method of claim 1 in which the cross-sectional area of the shaft is reduced between 8% and 20% of the unreduced cross-sectional area of the shaft.

7. The method of claim 1 in which there is a taper at each end of the reduced cross-section of the shaft.

* * * * *